United States Patent [19]

Gennari

[11] Patent Number: 5,114,931

[45] Date of Patent: May 19, 1992

[54] INJECTABLE THERAPEUTIC COMPOSITIONS CONTAINING STABLE S-ADENOSYL-L-METHIONINE SALTS

[75] Inventor: Federico Gennari, Truccazzano, Italy

[73] Assignee: Bioresearch S.p.A., Milan, Italy

[21] Appl. No.: 784,855

[22] Filed: Oct. 4, 1985

Related U.S. Application Data

[63] Continuation-in-part of Ser. No. 637,054, Aug. 2, 1984.

[30] Foreign Application Priority Data

Aug. 24, 1983 [IT] Italy .................. 22623 A/83

[51] Int. Cl.$^5$ .......................... C07H 19/167
[52] U.S. Cl. .......................... 514/46; 514/45; 536/26; 536/24
[58] Field of Search .................. 536/24, 26

[56] References Cited

U.S. PATENT DOCUMENTS 3,893,999  7/1975  Fiecchi .................. 536/26

FOREIGN PATENT DOCUMENTS 0041898  3/1983  Japan .................. 536/26

OTHER PUBLICATIONS

Ikezuki et al., Chem. Abstr., 71:94778a, 1969 (Ger. Patent #1,808,948).
Okazaki et al., Chem. Abstr., 83:152337s, 1975.
Good et al., Chem. Abstr., 64:10068b, 1966.

*Primary Examiner*—Johnnie R. Brown
*Assistant Examiner*—L. Eric Crane
*Attorney, Agent, or Firm*—Stevens, Davis, Miller & Mosher

[57] ABSTRACT

The invention discloses injectable therapeutic compositions containing stable S-adenosyl-L-methionine (SAMe) salts as an active ingredient. Injectable therapeutic compositions which permit large doses of SAMe to be administered by injection, at physiological pH having excellent tolerability has been achieved by administering SAMe salts in an aqueous solution which is adjusted to a pH of between 5 and 8.5 containing an amino acid and an alkaline base in critical proportions.

4 Claims, No Drawings

INJECTABLE THERAPEUTIC COMPOSITIONS CONTAINING STABLE S-ADENOSYL-L-METHIONINE SALTS

This is a continuation-in-part of application Ser. No. 637,054 filed Aug. 2, 1984.

This invention relates to new injectable therapeutic compositions containing stable S-adenosyl-L-methionine salts as active principle. Sulpho-adenosyl-L-methionine (I) is known to be the main biological donor of methyl groups.

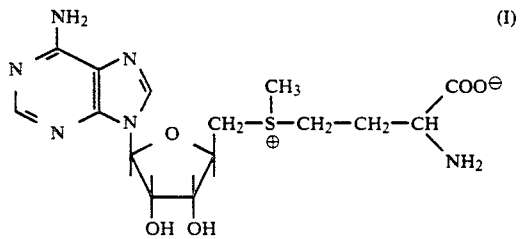

S-adenosyl-L-methionine (hereinafter referred to as SAMe) is a physiologically active substance which plays an important role as a methyl group donor of methylation reaction by way of various transmethylases in living organisms.

This special characteristic has made it the subject of considerable interest, initially from the biochemical aspect and subsequently for its therapeutic applications.

Sulpho-adenosyl-L-methionine (SAMe) is currently widely used in various fields of human therapy.

The therapeutic value for hepatopias, hyperdislipidemias, generalized or local arteriosclerosis, psychiatric manifestations of depressive and neurological type, degenerative arthromathies, neurological algic manifestation, disturbance of the sleeping-waking rhythm, etc. have been reported.

The therapeutic use of SAMe has required the solution of large problems which for many years were considered insuperable, namely its instability at ambient temperature and the complexity of its preparation and purification, which have been difficult to implement on an industrial scale.

These problems have been solved by the present inventor. The present application together with numerous other patents U.S. Pat. Nos. 3,893,999, 3,954,726 and 4,057,686, and European patent application 82107333.5) relating to thermally stable SAMe salts and the industrial processes for their preparation are commonly assigned.

The stable SAMe salts of the aforesaid patents have all given excellent results in human therapy, but have the great drawback of very high acidity, as is necessary for SAMe stabilisation, so that in its injectable forms the active principle, generally in lyophilised form, must be accompanied by a suitable buffer solvent which adjusts the pH of the final solution to within physiological values.

This problem has been confronted in the past by using phosphate buffers. In addition, because phosphate buffers give rise to local pain problems, lidocaine has been added to the compositions as a local anesthetic.

However, the considerably increasing clinical use of SAMe salts has shown the need for a large increase in dosage, which has passed from the initial 20–100 mg/day to 500–600 mg/day (expressed as SAMe ion).

Consequently, the initial injectable formulations containing 15 mg of SAMe ion have grown to injectable formulations containing 200 mg of SAMe ion.

For such high SAMe ion quantities, the use of phosphate buffers has proved completely unsuitable from the local pain aspect, in spite of increase in the lidocaine.

The object of the present invention is to provide new injectable therapeutic compositions which enable large doses of SAMe to be administered by injection, at physiological pH with excellent tolerability, while dispensing with lidocaine or other local anesthetics, which could cause side-effects.

In this respect, it has been surprisingly found possible to attain the aforesaid object by administration stable SAMe salts in an aqueous solution which is adjusted to a pH of between 5 and 8.5 and contains an amino acid and an alkaline base in well defined critical proportions.

According to the invention, either basic or non-basic amino acids can be used.

Of the basic amino acids, lysine, ornithine and arginine have proved of particular interest, whereas of the non-basic amino acids glycine, alanine, phenylalanine, serine, valine, leucine, isoleucine and proline are preferred.

Lysine is preferably used because of its low cost, easy availability, very low toxicity and lack of pharmacological or therapeutic effects attributable to it, particularly at the low dosage used.

According to the present invention, the basic amino acid is used in a molar proportion of between 3:1 and 5:1 with respect to the SAMe ion, and preferably 4:1, and sodium hydroxide is used in a molar proportion of between 0.2:1 and 1:1 with respect to the SAMe ion, and preferably 0.5:1.

If a non-basic amino acid is used, it is used in a molar proportion of between 3:1 and 10:1 with respect to the SAMe, and preferably 6.5:1, in which case the alkaline base is used in a molar proportion of between 3:1 and 6:1, and preferably 4.5:1 with respect to the SAMe.

Preferably, the new injectable therapeutic compositions are packaged into two separate vials, one containing the stable SAMe salt generally in lyophilised form, and the other containing the amido acid, the alkaline base and water. The water volume is generally between 2 and 30 ml, and generally 5 ml per vial. The pH of the vial containing the solvent composition is between 10 and 10.5.

Summarising, the new injectable therapeutic compositions have the following advantages:
1. they dispense with the lidocaine or other local anesthetic, with consequent elimination of possible side-effects due to these;
2. the vials are suitable both for intramuscular and intravenous use, thus dispensing with the need for distinguishing the two products;
3. renal toxicity is no longer applicable;
4. local pain, also due to phosphates, is eliminated;
5. the pharmacological dose can be considerably increased.

The following examples describe some pharmaceutical compositions based on the new invention, however these examples are purely illustrative in character and do not limit the invention itself.

EXAMPLE 1

Injectable pharmaceutical compositions containing stable S-adenosyl-L-methionine salts together with lysine-sodium hydroxide as buffer agent.

| (A) | A lyophilised vial contains: | |
|---|---|---|
| | SAMe disulphate-p.toluenesulphonate | 193 mg |
| | equivalent to SAMe ion | 100 mg |
| | A solvent vial contains: | |
| | Lysine | 150 mg |
| | Sodium hydroxide | 4.5 mg |
| | Water for injectable solutions, remainder to | 5 ml |

The pH value of the obtained injectable solution is 7.2.

| (B) | A lyophilised vial contains: | |
|---|---|---|
| | SAMe disulphate di-p.toluenesulphonate | 471 mg |
| | equivalent to SAMe ion | 200 mg |
| | A solvent vial contains: | |
| | Lysine | 300 mg |
| | Sodium hydroxide | 9 mg |
| | Water for injectable solutions, remainder to | 5 ml |

The pH value of the obtained injectable solution is 6.5.

| (C) | A lyophilised bottle contains: | |
|---|---|---|
| | SAMe 2,5 sulphate | 646 mg |
| | equivalent to SAMe ion | 400 mg |
| | A solvent vial contains: | |
| | Lysine | 600 mg |
| | Sodium hydroxide | 18 mg |
| | Water for injectable solution, remainder to | 15 ml |

The pH value of the obtained injectable solution is 7.2.

EXAMPLE 2

Injectable pharmaceutical compositions containing stable S-adenosyl-L-methionine salts, together with glycine-sodium hydroxide as buffer agent.

| (A) | A lyophilised vial contains: | |
|---|---|---|
| | SAMe disulphate-p.toluenesulphonate | 193 mg |
| | equivalent to SAMe ion | 100 mg |
| | A solvent vial contains: | |
| | Glycine | 100 mg |
| | Sodium hydroxide | 45 mg |

The pH value of the obtained injectable solution is 6.8.

| (B) | A lyophilised vial contains: | |
|---|---|---|
| | SAMe disulphate-di-p.toluenesulphonate | 471 mg |
| | equivalent to SAMe ion | 200 mg |
| | A solvent vial contains: | |
| | Glycine | 240 mg |
| | Sodium hydroxide | 90 mg |
| | Water for injectable solutions, remainder to | 5 ml |

The pH value of the obtained injectable solution is 6.2.

| (C) | A lyophilised bottle contains: | |
|---|---|---|
| | SAMe 2,5 sulphate | 646 mg |
| | equivalent to SAMe ion | 400 mg |
| | A solvent vial contains: | |
| | Glycine | 480 mg |
| | Sodium hydroxide | 180 mg |
| | Water for injectable solutions, remainder to | 15 ml |

The pH value of the obtained injectable solution is 6.7.

EXAMPLE 3

Injectable pharmaceutical compositions containing stable S-adenosyl-L-methionine salts, together with ornithine-sodium hydroxide as buffer agent.

| (A) | A lyophilised vial contains: | |
|---|---|---|
| | SAMe disulphate-p.toluenesulphonate | 193 mg |
| | equivalent to SAMe ion | 100 mg |
| | A solvent vial contains: | |
| | Ornithine | 136 mg |
| | Sodium hydroxide | 4.5 mg |
| | Water for injectable solutions, remainder to | 5 ml |

The pH value of the obtained injectable solution is 7.1.

| (B) | A lyophilised vial contains: | |
|---|---|---|
| | SAMe disulphate-di-p.toluenesulphonate | 471 mg |
| | equivalent to SAMe ion | 200 mg |
| | A solvent vial contains: | |
| | Ornithine | 275 mg |
| | Sodium hydroxide | 9 mg |
| | Water for injectable solutions, remainder to | 5 ml |

The pH value of the obtained injectable solution is 6.3.

| (C) | A lyophilised bottle contains: | |
|---|---|---|
| | SAMe 2,5 sulphate | 646 mg |
| | equivalent to SAMe ion | 400 mg |
| | A solvent vial contains: | |
| | Ornithine | 545 mg |
| | Sodium hydroxide | 18 mg |
| | Water for injectable solutions, remainder to | 10 ml |

The pH value of the obtained injectable solution is 7.2.

EXAMPLE 4

Injectable pharmaceutical compositions containing stable S-adenosyl-L-methionine salts, together with arginine/sodium hydroxide as buffer agent

| (A) | A lyophilized vial contains: | |
|---|---|---|
| | SAMe di-sulphate-di-p.toluenesulphonate | 236 mg |
| | equivalent to SAMe ion | 100 mg |
| | A solvent vial contains: | |
| | Arginine | 100 mg |
| | Sodium hydroxide | 4.5 mg |
| | Water for injectable solutions, remainder to | 5 ml |

The pH value of the obtained injectable solution is 6.5.

| (B) | A lyophilised vial contains: | |
|---|---|---|
| | SAMe di-sulphate-p.toluenesulphonate | 386 mg |
| | equivalent to SAMe ion | 200 mg |
| | A solvent vial contains: | |

-continued

| | |
|---|---|
| Arginine | 200 mg |
| Sodium hydroxide | 9 mg |
| Water for injectable solutions, remainder to | 5 ml |

The pH value of the obtained injectable solution is 7.5.

| (C) | A lyophilised bottle contains: | |
|---|---|---|
| | SAMe 2,5 sulphate | 646 mg |
| | equivalent to SAMe ion | 400 mg |
| | A solvent vial contains: | |
| | Arginine | 400 mg |
| | Sodium hydroxide | 18 mg |
| | Water for injectable solutions, remainder to | 10 ml |

The pH value of the obtained injectable solutions is 7.5

EXAMPLE 5

Injectable pharmaceutical compositions containing stable S-adenosyl-L-methionine salts, together with alanine/sodium hydroxide as buffer agent

| (A) | A lyophilised vial contains: | |
|---|---|---|
| | SAMe 2,5 sulphate | 162 mg |
| | equivalent to SAMe ion | 100 mg |
| | A solvent vial contains: | |
| | Alanine | 140 mg |
| | Sodium hydroxide | 45 mg |
| | Water for injectable solutions, remainder to | 5 ml |

The pH value of the obtained injectable solutions is 6.9.

| (B) | A lyophilised vial contains: | |
|---|---|---|
| | Di-sulphate-di-p.toluenesulfonate | 471 mg |
| | equivalent to SAMe ion | 200 mg |
| | A solvent vial contains: | |
| | Alanine | 280 mg |
| | Sodium hydroxide | 90 mg |
| | Water for injectable solutions, remainder to | 5 ml |

The pH value of the obtained injectable solutions is 6.2.

| (C) | A lyophilised bottle contains: | |
|---|---|---|
| | SAMe di-sulphate-p.toluenesulfonate | 772 mg |
| | equivalent to SAMe ion | 400 mg |
| | A solvent vial contains: | |
| | Alanine | 560 mg |
| | Sodium hydroxide | 180 mg |
| | Water for injectable solutions, remainder to | 15 ml |

The pH value of the obtained injectable solution is 6.8.

EXAMPLE 6

Injectable pharmaceutical compositions containing stable S-Adenosyl-L-methionine salts, together with serine/sodium as buffer agent

| (A) | A lyophilised vial contains: | |
|---|---|---|
| | SAMe di-sulphate-p.toluenesulfonate | 193 mg |
| | equivalent to SAMe ion | 100 mg |
| | A solvent vial contains: | |
| | Serine | 170 mg |
| | Sodium hydroxide | 45 mg |
| | Water for injectable solutions, remainder to | 5 ml |

The pH value of the obtained injectable solution is 6.8.

| (B) | A lyophilised vial contains: | |
|---|---|---|
| | SAMe di-sulphate-di-p.toluenesulfonate | 471 mg |
| | equivalent to SAMe ion | 200 mg |
| | A solvent vial contains: | |
| | Serine | 340 mg |
| | Sodium hydroxide | 90 mg |
| | Water for injectable solutions, remainder to | 5 ml |

The pH value of the obtained injectable solution is 6.1

| (C) | A lyophilised bottle contains: | |
|---|---|---|
| | SAMe 2,5 sulphate | 646 mg |
| | equivalent to SAMe ion | 400 mg |
| | A solvent vial contains: | |
| | Serine | 680 mg |
| | Sodium hydroxide | 180 mg |
| | Water for injectable solutions, remainder to | 15 ml |

The pH value of the obtained injectable solution is 6.6.

I claim:

1. Injectable therapeutic aqueous compositions containing stable S-adenosyl-L-methionine (SAMe) salts, including 100–500 mg of SAMe salt (expressed as SAMe ion per vial and sodium hydroxide in a molar proportion of between 0.2:1 and 1:1 with respect to the SAMe ion and an amino acid selected from the group consisting of lysine, arginine and ornithine, in a molar proportion of between 3:1 and 5:1 with respect to the SAMe ion, said aqueous composition having a pH between 5 and 8.5.

2. Injectable therapeutic compositions of claim 1, wherein said sodium hydroxide is present in a molar proportion between 0.5:1 and said amino acid in a molar proportion of 4:1 with respect to the SAMe ion.

3. Injectable therapeutic aqueous compositions containing stable S-adenosyl-L-methionine salts, characterised by comprising sodium hydroxide in a molar proportion of between 3:1 and 6:1 with respect to the SAMe ion and an amino acid selected from the group consisting of glycine, alanine and serine, in a molar proportion of between 3:1 and 10:1 with respect to the SAMe ion, said aqueous composition having a pH between 5 and 8.5.

4. Injectable therapeutic compositions of claim 3, wherein said sodium hydroxide is present in a molar proportion of 4.5:1 and said amino acid in a molar proportion of 6.5:1.

* * * * *